(12) United States Patent
Pal et al.

(10) Patent No.: US 6,528,264 B1
(45) Date of Patent: Mar. 4, 2003

(54) POLYMER SUPPORT FOR DNA IMMOBILIZATION

(75) Inventors: Santona Pal, Painted Post, NY (US); Joydeep Lahiri, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 96 days.

(21) Appl. No.: 09/704,013

(22) Filed: Nov. 1, 2000

(51) Int. Cl.[7] .......................... C12Q 1/68; C12P 19/34; C12M 1/34; C07H 21/02; C07H 21/04

(52) U.S. Cl. .......................... 435/6; 435/7.1; 435/91.1; 435/91.2; 435/287.2; 536/22.1; 536/23.1; 536/24.3; 536/24.31; 536/24.32; 536/24.33

(58) Field of Search .......................... 435/6, 7.1, 91.1, 435/91.2, 287.2; 536/22.1, 23.1, 24.3–37

(56) References Cited

U.S. PATENT DOCUMENTS

| | | | | |
|---|---|---|---|---|
| 5,935,793 A | * | 8/1999 | Wong | 435/6 |
| 5,959,098 A | * | 9/1999 | Goldberg et al. | 536/25.3 |
| 6,159,695 A | * | 12/2000 | McGovern et al. | 435/6 |
| 6,287,768 B1 | * | 9/2001 | Chenchik et al. | 435/6 |

* cited by examiner

*Primary Examiner*—Jeffrey Siew
(74) *Attorney, Agent, or Firm*—Thomas R. Beall (57) ABSTRACT

This invention relates to substrates for use in immobilizing biomolecules. More particularly, the invention relates to substrates (e.g. glass slides) having a coating of polylysine covalently attached to a silane layer coating the slide, wherein the polylysine compound has a functional $NH_2$ group which can be coupled directly, indirectly, covalently, or non-covalently to a biomolecule (e.g., a DNA or RNA molecule). Even more particularly, the invention relates to specific prescribed addition of ethanalomine to the polylysine thereby forming a mixture which dramatically enhances the effectiveness of the polylysine for immobilizing DNA. Among other applications, the polylysine coated substrates can be used in the preparation of high density arrays for performing hybridization assays

45 Claims, 8 Drawing Sheets

(5 of 8 Drawing Sheet(s) Filed in Color)

CHANNEL 1 CHANNEL 2 MOLAR RATIO polyK : EA S/N

CHANNEL 1 CHANNEL 2 MOLAR RATIO polyK : EA S/N

CHANNEL 1 CHANNEL 2 MOLAR RATIO polyK : EA S/N

CHANNEL 1 CHANNEL 2 MOLAR RATIO polyK : EA S/N

CHANNEL 1  CHANNEL 2

FIG. 6B

CHANNEL 1  CHANNEL 2

FIG. 6C

CHANNEL 1  CHANNEL 2

FIG. 6D

CHANNEL 1  CHANNEL 2

POLYMER SUPPORT FOR DNA IMMOBILIZATION

FIELD OF INVENTION

This invention relates to substrates for use in immobilizing biomolecules. More particularly, the invention relates to substrates (e.g. glass slides) having a coating of polylysine covalently attached to a silane layer coating the slide, wherein the polylysine compound has functional $NH_2$ groups which can be used to either directly immobilize biomolecules (e.g. DNA molecules), covalently, or non-covalently; or be used for attachment of linkers for subsequent immobilization of biomolecules. Even more particularly, the invention relates to specific prescribed addition of ethanalomine to the polylysine thereby forming a mixture which dramatically enhances the effectiveness of the polylysine for immobilizing DNA. Among other applications, the polylysine coated substrates can be used in the preparation of high density arrays for performing hybridization assays.

BACKGROUND OF THE INVENTION

Polylysine coatings have been utilized for years in the modification of glass and plastic in order to create a biocompatible surface for cell attachment. Additionally, polylysine has been utilized as a coating that will immobilize biomolecules such as DNA for use in hybridization assays. The DNA is held to the surface by electrostatic forces between the positively charged side chain of the polylysine and the net negative charge of the DNA molecule. Polylysine has several advantages over other popular DNA attachment chemistries such as gamma-aminopropyltriethoxysilane (GAPS). For one, polylysine functionalizes a substrate surface with a greater concentration of amino groups than GAPS, which in turn results in greater retention of DNA. Second, the polylysine molecule, when attached to a substrate, is flexible and extends from the surface, and therefore is more suitable for the binding and hybridization of large polymeric molecules such as DNA.

Unfortunately, Polylysine is not very stable on glass substrates. As a polycation, it electrostatically interacts with the negatively charged surface of the glass. However, a common step in any DNA hybridization assay is a blocking step, which is used to block any non-specific binding of the sample DNA probes. For example, succinic anhydride, a commonly used blocking agent confers a net negative charge to the polylysine. This effectively blocks the non-specific DNA sample binding, but also has the effect of weakening the electrostatic attachment of the polylysine to the glass surface.

The present invention presents a surface coating method and attachment chemistry which takes advantage of the benefits of polylysine while obviating the problem of its inherent instability by covalently attaching the polylysine to the glass by means of a silane compound.

SUMMARY OF INVENTION

The present invention discloses a coating that when applied to a substrate surface, allows for the effective immobilization of biomolecules. The coating comprises a silane layer covalently attached to the substrate and a polycation covalently attached to the silane layer. The polycationic layer possesses functionalities that will immobilize biomolecules.

The present invention further discloses mixing the polycation with an auxiliary nucleophile that has the effect of controlling the amount of covalent attachment of the polycation to the substrate surface. In a specific example, an optimal ratio range of the polylysine (polycation) and ethanolamine (auxiliary nucleophile) mixture has been identified.

The present invention further discloses a high density nucleic acid array whereby different known genetic sequences are attached at a plurality of locations to a substrate having a silane layer covalently attached to the substrate surface and a polycation layer covalently attached to the silane layer. The gene sequences are electrostatically attached to the polycation layer. Again, the effectiveness of the polycationic layer to immobilize the DNA may be modulated by selective addition of an auxiliary nucleophile diluent such as ethanalomine.

The present invention also discloses a method of preparing a substrate for biomolecular immobilization comprising the steps of: providing a substrate with a surface; attaching a silane layer to the surface; mixing a functionalizes polymer with a diluent to form a mixture; and, attaching the mixture to the silane coated substrate. A further embodiment provides for the attachment of biomolecules (e.g., DNA, RNA, proteins, antigens, ligands, haptens, etc.) to the substrate via the functionality of the cationic polymer.

Still another embodiment calls for chemical modification of the polycationic layer to create reactive esters at the surface. These reactive esters have the ability to covalently attach various ligands.

BRIEF DESCRIPTION OF THE DRAWINGS

The patent application file contains at least one page of drawings executed in color. Copies of this patent or patent application publication with color drawings will be provided by the U.S. Patent and Trademark Office upon request and payment of the necessary fee.

DETAILED DESCRIPTION OF THE INVENTION

Figure 1:
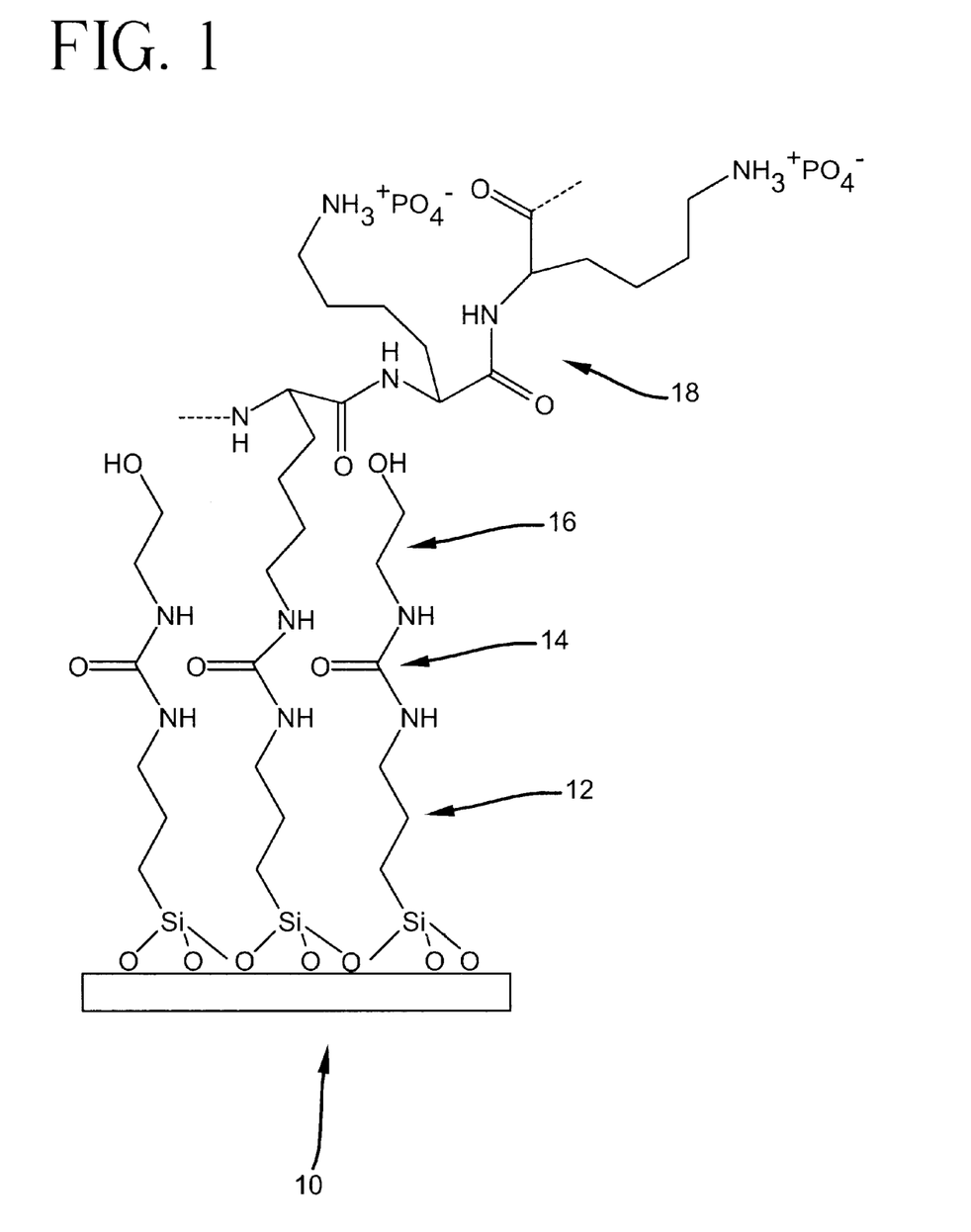
FIG. 1 is a chemical representation of the support of the present invention.

FIG. 1 shows a chemical representation of one embodiment of the present invention. A glass substrate 10 is coated with silane molecules, preferably and as in FIG. 1, gamma-isocyanatopropylsilane (GIPS) 12. The silane molecules 12 have the ability to cross-link into a three-dimensional structure via their tri-functional silanol groups. Siloxane bonds may be formed between the silane. e.g. a GIPS molecule, and the substrate surface. Alternatively, siloxane bonds may be formed between silane molecules. In the latter case, the silane molecules may form a three dimensional cross-linked structure several molecules thick. This may constitute a layer having a thickness in the domain of a 4 monolayer provided that the final thickness is not more than 10 molecules. Although not wishing to be bound by any particular theory of operation, it is believed that in the case of GIPS film on glass, the thickness is in the order of 10 nanometers and the molecules are cross-linked into a three dimensional structure covalently grafted to the glass surface.

Based upon the type of silane chosen, it should be noted that various functional groups may be exposed at the surface including, without limitation, primary amines. propyl hydrocarbon chain segments, silanol groups, and siloxide bonds. In FIG. 1, it is generally assumed that the isocyanto functionality 14 covalently attaches both ethanalomine molecules 16 as well as polylysine molecules 18 by means of a strong urea linkage. The key breakthrough is that unlike traditional polylysine coated slides, the polylysine is covalently coupled to the substrate via the GIPS molecule. This creates an extremely durable and stable attachment that allows the polylysine to remain attached to the slide through all of the blocking steps and hybridization experiments. The positively charged side chain of the polylysine molecule, which extends out from the substrate surface, allows for the electrostatic immobilization of negatively charged biomolecules such as DNA.

The ethanalomine molecules 16 compete with the polylysine 18 at the isocyanto functional binding sites. This competition creates a surface in which the polylysine groups are selectively spaced apart. This is important because the biomolecules. (e.g. DNA) that attach and are immobilized to the polylysine will also be spaced at a controlled distance, thereby limiting steric hindrance encountered by a sample molecule. (e.g. complimentary strand of DNA) during hybridization experiments. As shown in the experimental section, the spacing has a marked effect on DNA hybridization. Altering the polylysine/ethanalomine molar ratio prior to application to the silane coated glass surface has the effect of controlling the spacing between polylysine molecules.

For polylysine with a molecular weight of approximately 7500, the preferred polylysine/ethanolamine molar ratio range is between 1:1 and 1:250. and more preferably between 1:100 and 1:150. Even more preferably the polylysine/ethanalomine molar ratio is approximately 1:120.

Figure 2:
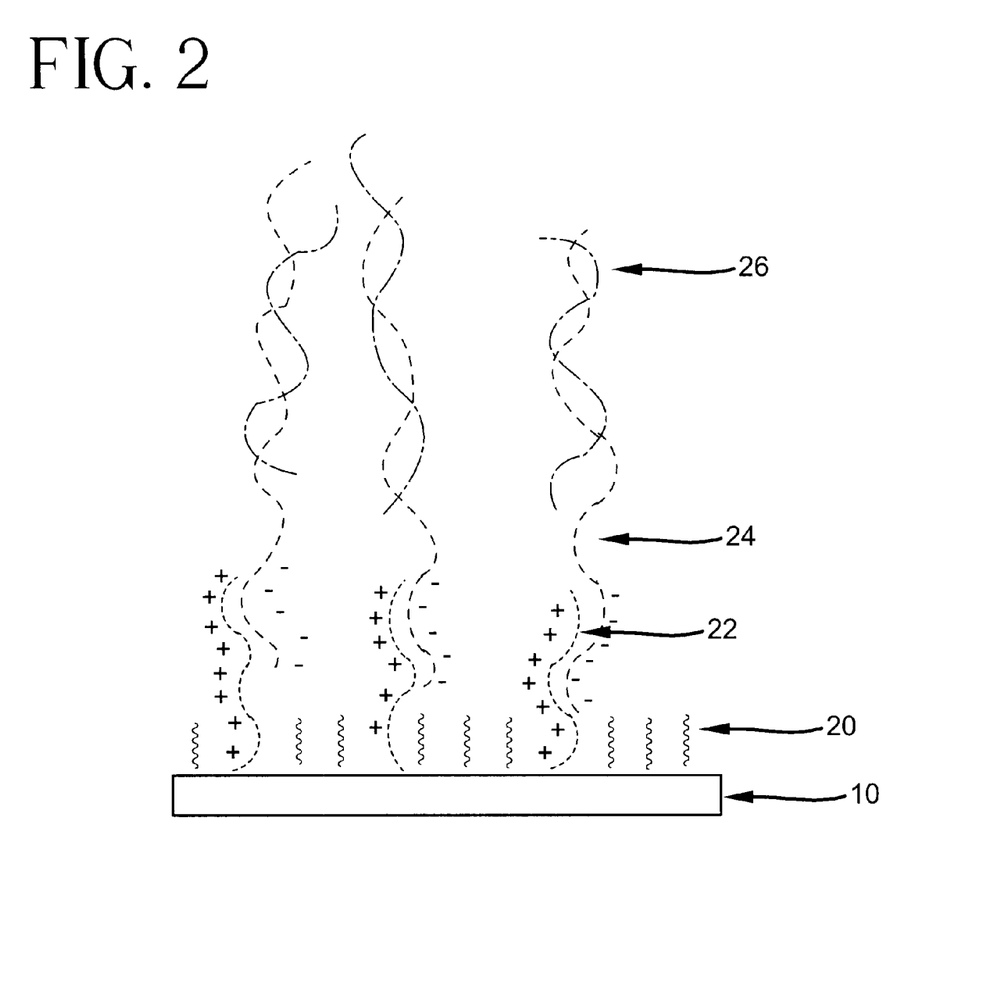
FIG. 2 is a schematic representation of the support of the present invention.

FIG. 2 demonstrates the effectiveness of the lateral spacing effect generated by the ethanalomine diluent. The substrate 10 has attached to its surface, via the silane covalent linkage, polylysine molecules 22 showing a positive charge, spaced by neutral ethanalomine molecules 20. Probe DNA molecules 24, having a net negative charge, are electrostatically immobilized by the polylysine 22. Target DNA molecules 26 are hybridized to the immobilized DNA molecules 24. The spacing between polylysine molecules 22 allowed by the ethanalomine 20 creates lateral spacing between immobilized probe DNA 24 which in turn allows for the target DNA 26 to freely access the probe DNA and hybridize.

Although a preferred embodiment has been described, it should be noted that various substitutes for the components of the present invention exist. For example, the substrate preferably is an inorganic solid made of either porous or non-porous glass, and more preferably., an alkaline earth aluminoborosilicate glass. However, the substrate may be any inorganic material, organic plastic material, or metalized surface that either naturally contains amine reactive functional groups or has been modified in some way to contain functional groups that will covalently attach a cationic polymer. Examples of materials which can form the substrate include silica, aluminum oxide. titanium oxide, metals with an oxide layer, and glasses of various types, e.g. soda-lime, boro silicate, and boro-alumino silicate glasses.

Likewise, the substrate may embody a variety of forms. The substrate will have an exposed surface. In the preferred embodiment, the substrate takes the form of a 1"×3" flat glass slide suitable for immobilizing an array of nucleotides, proteins or cells thereupon. Normally, at least part of the exposed surface will be planar, as in the preferred embodiment, although curved surfaces can be treated in accordance with the present invention. e.g. the working surface can be formed on the inside surface of a test tube or well from a multiwell plate or the outside of a bead.

A variety of silanes may be used in the practice of the present invention. The general structural formula for a silane is $R_nSiX_{4-n}$, where R is an organic group and X is a hydrolysable group such as a chlorine atom or an alkoxy group. The value of n is an integer in the range of 1 to 3, more preferably 2 than 3, and most preferably 1. Although a mixture of silanes can be used if desired, a single silane is preferred. Examples of suitable silanes used in the practice of the present invention include isocyantoalkylsilanes, succinic anhydridealkylsilanes, glycidoxyalkylsilanes, and epoxyalkylsilanes. Gamma-isocyanatopropylsilane is used commensurate with the preferred embodiment of the invention.

Further, a variety of polyamino functionalized polymers may be employed in the present invention to covalently attach to the silane molecules on one end and to immobilize biomolecules on the other. Examples of polyamino functionalized polymers include polylysine, polyarginine, polyethyleneimine, aminated polysaccharides, aminated oligosaccharides, other polyamino amines, amino carboxylated oligosaccharides, polypeptides, and polyaminoalcohols. Polylysine is the functionalized polymer of choice in the preferred embodiment of the invention.

Ethanalomine, as previously described, is used as a diluent to be mixed with the polyamino functionalized polymer for selectively spacing immobilized probe molecules. Preferably, the diluent has no molecular charge and will covalently react with a silane. Examples of proper diluents for use with the present invention include sarcosine, glycine, oligo (ethylene glycol)-amine, and in the preferred embodiment, ethanalomine.

The substrate of the present invention serves to immobilize biomolecules which are in turn held as candidates for binding by entities which have a specific affinity for the immobilized biomolecule. For purposes of this invention, biomolecules shall represent biological or synthetic biomimetic molecules having a specific affinity for another molecule, through covalent or non-covalent interactions. Preferably, a specific biomolecule may contain (either by nature or by modification) functional groups (primary amine, sulfhydryl, aldehyde. etc.) a particular sequence (nucleic acids, amino acids or analogs), an epitope (antibody), a hapten or a ligand that allow it to covalently react or non-covalently bond to an entity on the surface of a substrate. Specific biomolecules include: deoxyribonucleic acids (DNA), ribonucleic acids (RNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates and haptens. The term "biomolecule" and "binding entity" are interchangeable for purposes of this disclosure.

Figure 4:
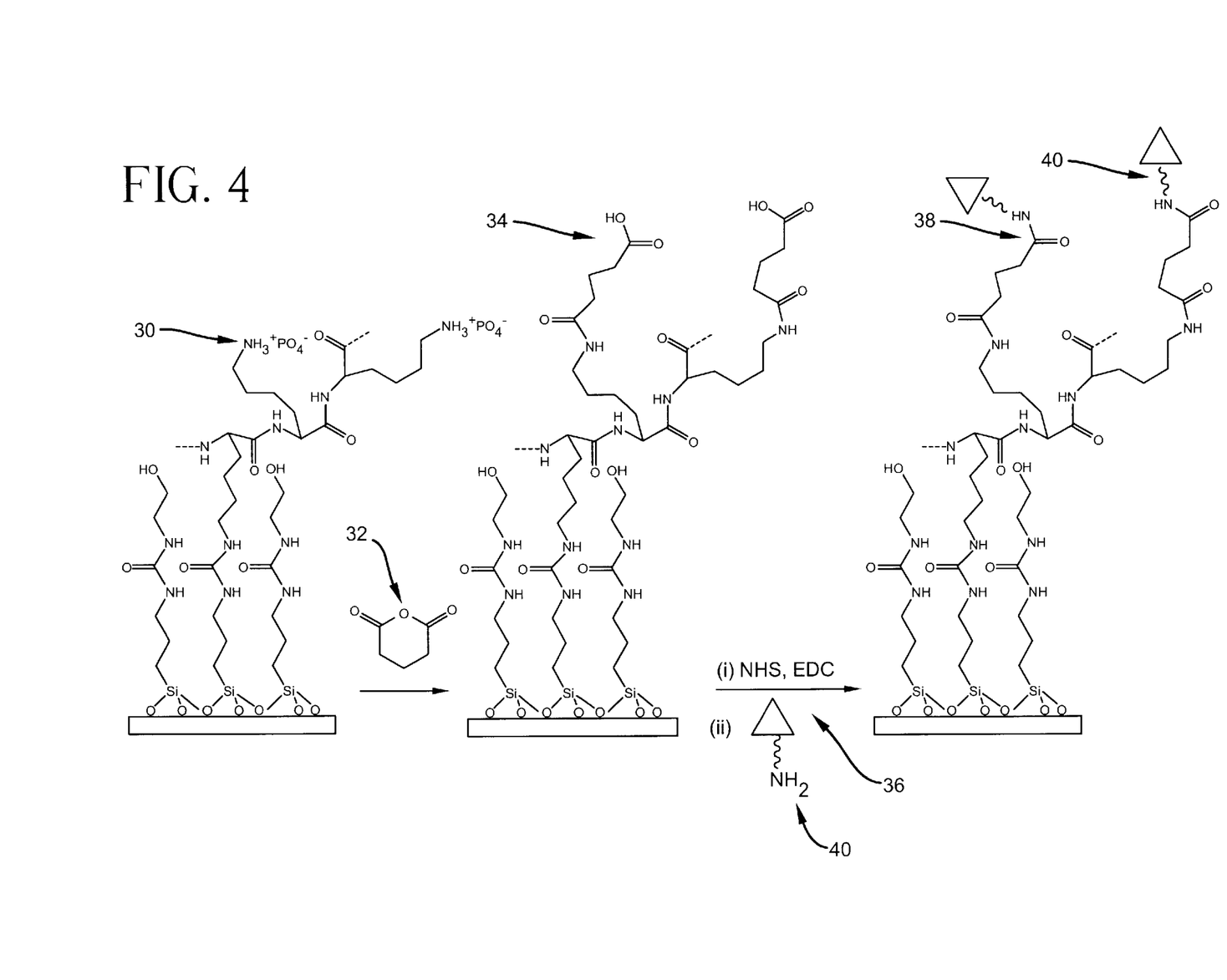
FIG. 4 is a chemical representation of the process of modifying the support of the present invention in order to form carboxyl group functionalities.

FIG. 4 is a schematic representation of the steps of a chemical reaction geared at modifying the substrate of FIG. 1 in order to induce covalent attachment of a ligand. A layer of GIPS 31 is covalently attached to a glass substrate 33. Polylysine molecules 35 and ethanolomine molecules 37 are covalently attached to the GIPS molecule via the urea linkage previously discussed. The lysine $\epsilon$-amino groups 30 are reacted with a cyclic anhydride 32 thereby producing a modified polylysine having extended carboxylic acid group functionalities 34. The carboxylic acid groups are then activated to form reactive esters by means of addition of N-hydroxysuccinimide (NHS) and N-ethyl-N'N'-dimethylaminopropyl-carbodimide (EDC) 36. The reactive esters allow for covalent attachment of ligands 40 by means of peptide bond formation 38. In this embodiment, the immobilization of the ligand is purely covalent.

EXAMPLE 1

Polylysine/Ethanalomine Molar Ratio Determines Ideal Signal to Noise Ratio

This example demonstrates by means of fluorescent false color imaging the effectiveness of the substrate of the present invention to retain DNA, hybridize DNA, and provide an acceptable signal to noise ratio.

The substrates used in this example were soda-lime glass microscope slides (Erie Scientific, Portsmouth, NH). All four slides used for the experiment were prepared in the following manner:

The glass slides were cleaned in 1M KOH solutions for 0.5 hour. After cleaning, the slides were rinsed in copious amounts of 18-ohm water, soaked in pure ethanol for 0.5 hour, and dried with nitrogen. Next, the slides were soaked in a silane solution consisting of 5% GIPS in isopropyl alcohol for approximately 2 hours in a humid chamber. The slides were then removed, briefly rinsed with isopropanol and deionized water respectively, and dried with nitrogen gas.

Four different baths of polylysine(7.5 kD)/ethanolmine in 10 mM sodium phosphate buffer (pH 9.5–10.0) were prepared according to the molar ratio concentrations listed in Table 1. Each slide was immersed in a corresponding bath solution for 45 minutes, then the slides were rinsed in deionized water and dried with nitrogen gas.

Probes in the form of Cy3 labeled 1.5 kb fragments of double stranded DNA at a concentration of 0.25 mg/ml, suspended in 50% dimethylsulphoxide: saline sodium citrate (DMSO:SSC) (150 mm sodium chloride; 15 mm sodium citrate) and labeled with Cy3 dye, were printed in a 5×5 matrix onto each slide. The slides were then washed and blocked with succinic anhydride.

Next, Cy5 labeled complimentary target DNA fragments were hybridized to the retained DNA using standard hybridization protocols (see, e.g. Eisen et al. 303 *Methods Enzymol.* 179–205 (1999). The hybridized slides were once again washed, dried with nitrogen and scanned using the General Scanning Scanner 3000 (at a laser power setting of 85. PMT setting of 60). The scanned image in channel 1 shows the amount of Cy3-labeled DNA retained and the image in channel 2 shows the amount of Cy5-labled DNA hybridized to the retained DNA.

Results

FIGS. 3A–D and Table I show the results of Experiment 1. FIGS. 3A–D each display sequential false color images from the fluorescence scan; the left image in each sequence represent the Cy3 detection. The intensity of signals indicates DNA probe retention; yellow and red indicates relatively higher retention, green and blue indicate less signal and lower retention levels (see FIG. 9). The right image in each sequence reflects Cy5 detection of the target indicating hybridization. Likewise, green images indicate relatively higher hybridization levels, while blue indicates lower levels of hybridization. Signal to noise ratio is measured as a ratio of the intensity of the signal from the labeled DNA to the signal intensity from the background areas.

Figure 3A:
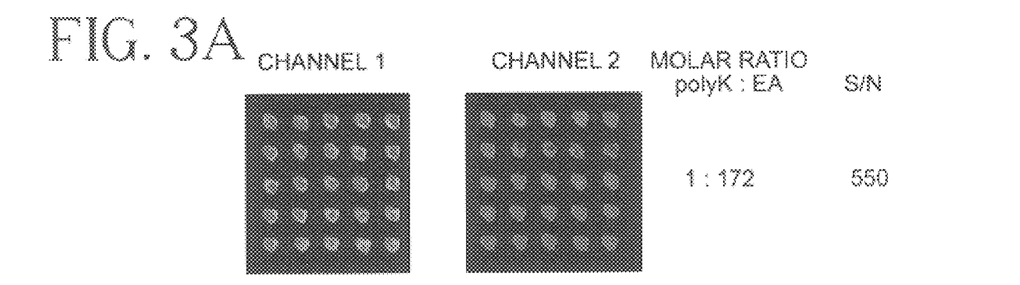
FIGS. 3A–3D are fluorescence false color images recording the retention (channel 1) of immobilized DNA and hybridization (channel 2) of sample DNA on substrates of the present invention having varying polylysine/ethanalomine molar ratios.
Figure 3B:
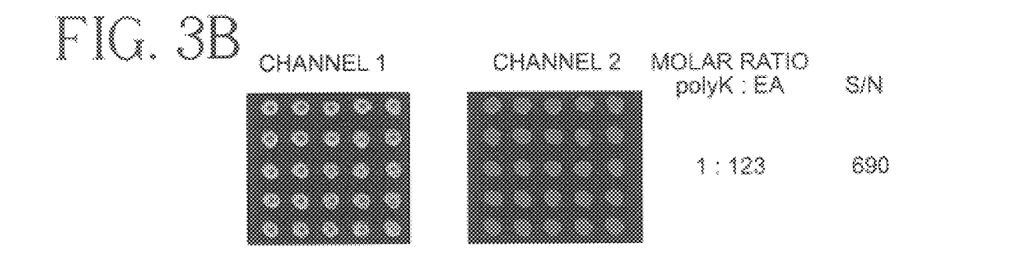
Figure 3C:
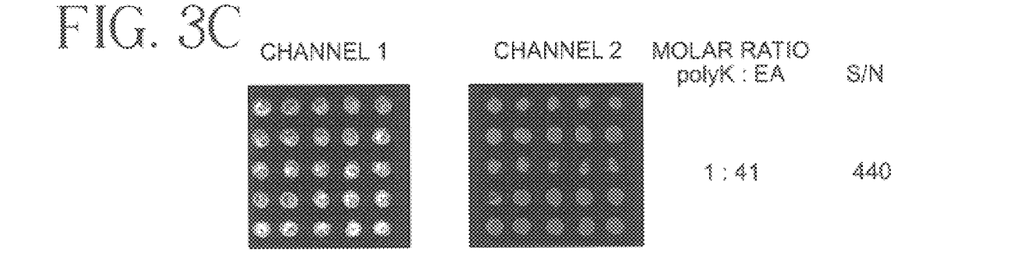
Figure 3D:
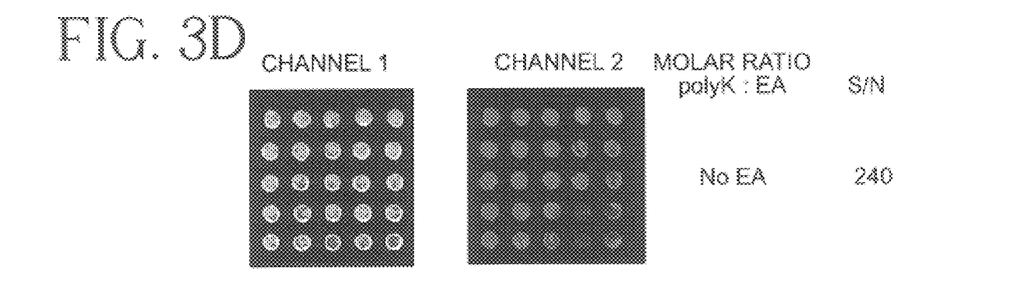

As can be readily observed, as the molar ratio of polylysine increases, signal intensity from the Cy3 labeled probe (FIGS. 3A–D, left side images) likewise increases. This, not surprisingly indicates that DNA retention increases as a function of polylysine concentration. However, signal intensity from the Cy5 labeled target (FIGS. 3A–D, right side images) increases from slide A to B, but decreases from slide B to slides C and D. This indicates that hybridization is optimized at a particular molar ratio of polylysine and ethanalomine. Further, as shown in Table 1, signal to noise ratio is optimized at a particular ratio of polylysine and ethanalomine. In the present experiment, the optimal molar ratio level of polylysine:ethanalomine for hybridization and signal to noise ratio, is 1:123, as demonstrated by slide B and as shown in FIG. 3B.

TABLE 1

| Slide | Molar Ratio (polylysine:ethanalomine) | Signal/Noise |
|---|---|---|
| A | 1:172 | 550 |
| B | 1:123 | 690 |
| C | 1:41 | 440 |
| D | No ethanalomine | 240 |

EXAMPLE 2

Covalent Attachment of DNA through Chemical Modification

This example demonstrates the hybridization efficiency of a substrate prepared through reactive group modifications of the polylysine molecule.

A single soda lime glass slide was cleaned in 1M KOH solutions for 0.5 hour. After cleaning, the slide was rinsed in copious amounts of 18-ohm water and soaked in pure ethanol for 0.5 hour, and dried with nitrogen. Next, the slide was soaked in a silane solution consisting of 5% GIPS in isopropyl alcohol for approximately 2 hours in a humid chamber. The slide was then removed, briefly rinsed with isopropanol and deionized water respectively, and dried with nitrogen gas.

A bath of polylysine(7.5 kD)/ethanolmine in 10 mM sodium phosphate buffer (pH 9.5–10.0) was prepared in a molar ratio of 1:120. The slide was then immersed in the bath solution for 45 minutes, rinsed in deionized water and dried with nitrogen gas.

Carboxylic acid functionalities were created by immersing the slide into to a solution prepared by first dissolving 1.66 grams of succinic anhydride in 105 ml of N-methyl pyrrolidone, and quickly adding in 11.66 ml of a 0.2M solution of sodiumborate (pH 8.0). After reacting for 10 minutes with gentle mixing, the slide was washed with water and dried with nitrogen gas.

Next, the slide was immersed in an aqueous solution of 11.5 mg/ml of N-hydroxysuccinimide (NHS) and 75.0 mg/ml of N-ethyl-N'N'-dimethyaminopropyl-carbodiimide (EDC) and allowed to react for 10 minutes under gentle mixing, followed by a water wash and nitrogen dried.

Probes in the form of single strand 25-mer oligonucleotides at a concentration of 1 mg/ml suspended in 50% dimethylsulphoxide: sodium citrate,(DMSO:SSC) were printed in a 5×5 matrix onto the slide. After washing and blocking, Cy5 labeled complimentary target DNA fragments were hybridized to the retained oligos using standard hybridization protocols. The slide was then washed and scanned for fluorescence using a General Scanning Scanner 3000 (GSI Lumonics. Billerica. Mass., USA) at a laser power setting of 85. and a PMT setting of 90. in order to detect s hybridization.

Result

Figure 5:
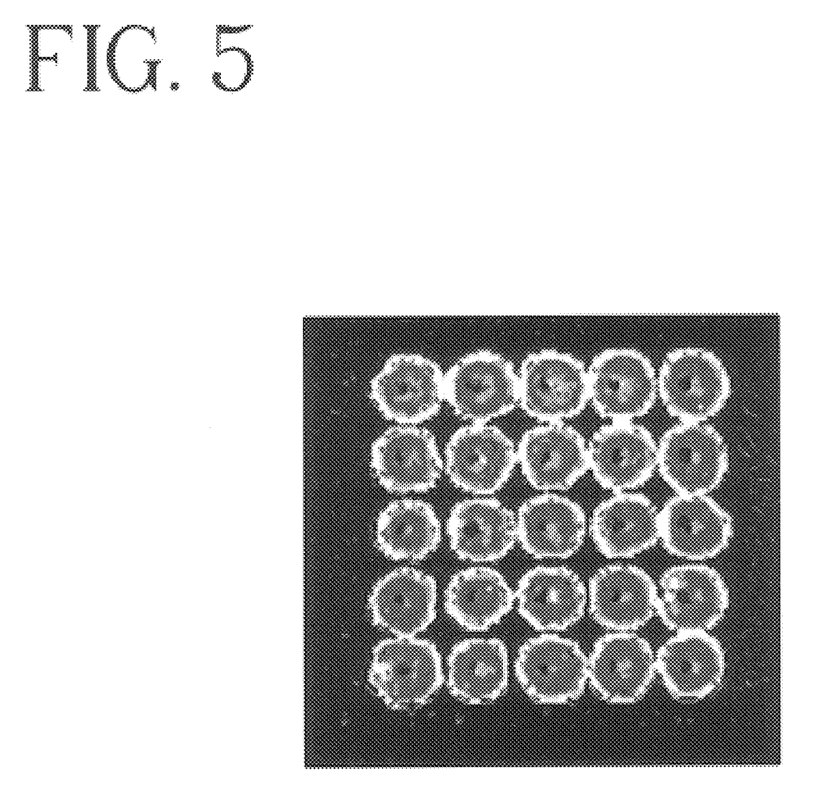
FIG. 5 is a false color fluorescence image recording hybridization occurring with amine terminated 25-mer oligonucleotide probes covalently bound to the support represented in FIG. 4.

FIG. 5 is a false color fluorescence image showing hybridization signal from the slide prepared as described above. The bright green/yellow coloration from the image indicates a strong signal thereby demonstrating efficient and detectable hybridization.

EXAMPLE 3

Influence of Molecular Weight of Polylysine on Soda Lime Glass and Porous glass.

This example demonstrates by means of fluorescent false color imaging the influence of the molecular weight of polylysine in DNA hybridization experiments over several substrates.

The substrates used in this example were soda-lime glass microscope slides (Erie Scientific. Portsmouth. N.H.) and porous glass slides (Vycor™, Corning Inc., Coming. N.Y.). The four slides used for the experiment, two of each substrate material, were prepared in the following manner:

The slides were cleaned in 1M KOH solutions for 0.5 hour. After cleaning, the slides were rinsed in copious amounts of 18-ohm water and soaked in pure ethanol for 0.5 hour, and dried with nitrogen. Next, the slides were soaked in a silane solution consisting of 5% GIPS in isopropyl alcohol for approximately 2 hours in a humid chamber. The slides were then removed, briefly rinsed with isopropanol and deionized water respectively, and dried with nitrogen gas.

Two different baths of polylysine/ethanolmine in 10 mM sodium phosphate buffer (pH 9.5–10.0) were prepared, one using polylysine having a molecular weight of 7.5 kD, the other using polylysine having a molecular weight of 40 kD The polylysine/ethanalomine molar ratio was approximately 1:120 for both baths. One flat glass slide and one porous glass slide were immersed into each-of the solutions for 45 minutes, the slides were then rinsed in deionized water and dried with nitrogen gas.

Probes in the form of 1.5 kb fragments of double stranded DNA at a concentration of 0.25 mg/ml, suspended in dimethylsulphoxide: sodium citrate (DMSO:SSC) and labeled with Cy3 dye, were printed in a 4×5 matrix onto each slide.

Next. Cy5 labeled complimentary target DNA fragments were hybridized to the retained DNA using standard hybridization protocols. In order to measure hybridization levels, the slides were once again washed, dried with nitrogen and scanned using the General Scanning Scanner 3000. The image scanned, in the Cy3 channel (channel 1) reflects the % retention of the printed DNA. Whereas, the image scanned in the Cy5 channel (channel 2) reflects the signal from hybridization.

Results

FIGS. 6A–D and Table 2 show the results of Experiment 3. FIGS. 6A–D each display sequential false color images from the fluorescence scan, the left image in each sequence represents the Cy3 detection after the probe DNA has been printed and the slide washed. The intensity of signal indicates DNA probe retention; yellow and green indicates relatively higher retention, purple and blue indicate less signal and lower retention levels. The right image in each sequence reflects Cy5 detection of the target indicating hybridization. Likewise, yellow and green images indicate relatively higher hybridization levels, while blue indicates lower levels of hybridization. Signal to noise ratio is measured as a ratio of the intensity of the signal from the labeled DNA to the signal intensity from the background areas.

Figure 6A:
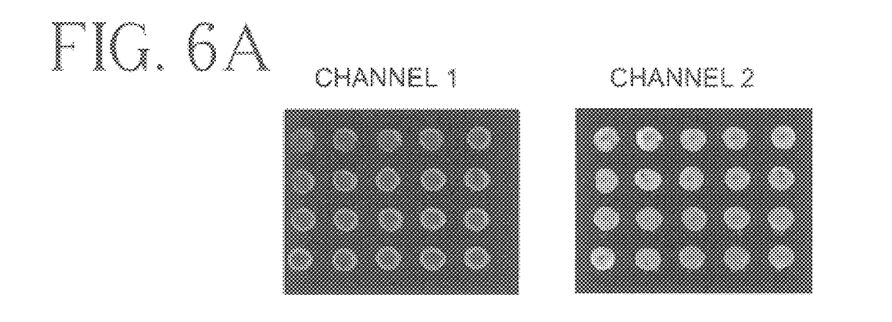
FIG. 6A are false color fluorescence images recording the retention (channel 1) of immobilized DNA and hybridization (channel 2) of sample DNA on a flat glass substrate of the present invention using polylysine having a molecular weight of 7.5 kD, mixed with ethanalomine.
Figure 6B:
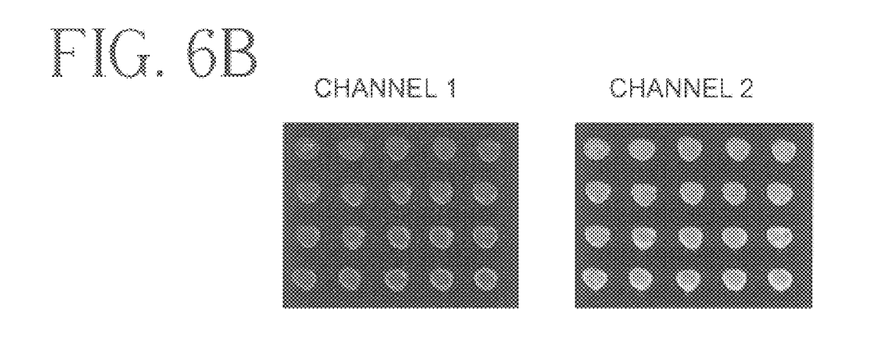
FIG. 6B are false color fluorescence images recording the retention (channel 1) of immobilized DNA and hybridization (channel 2) of sample DNA on a flat glass substrate of the present invention using polylysine having a molecular weight of 40 kD, mixed with ethanalomine.
Figure 6C:
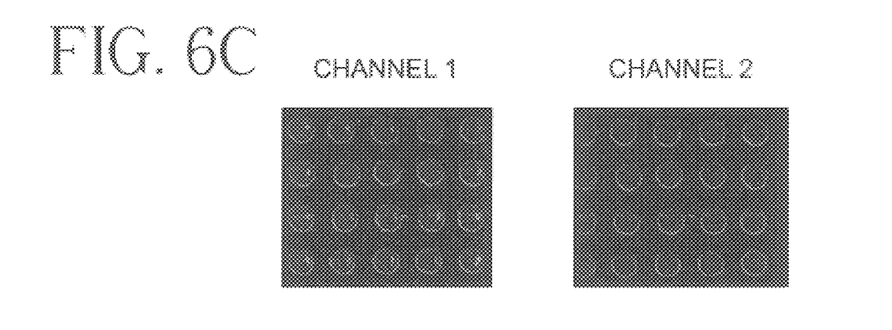
FIG. 6C are false color fluorescence images recording the retention (channel 1) of immobilized DNA and hybridization (channel 2) of sample DNA on a porous glass substrate of the present invention using polylysine having a molecular weight of 7.5 kD, mixed with ethanalomine.
Figure 6D:
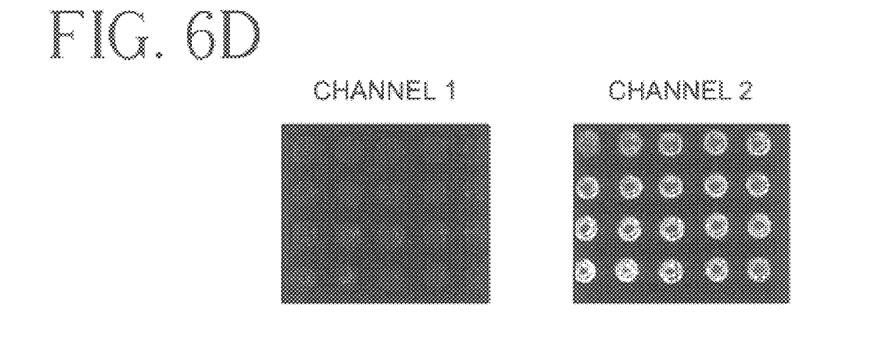
FIG. 6D are false color fluorescence images recording the retention (channel 1) of immobilized DNA and hybridization (channel 2) of sample DNA on a porous glass substrate of the present invention using polylysine having a molecular weight of 40 kD, mixed with ethanalomine.
Figure 7A:
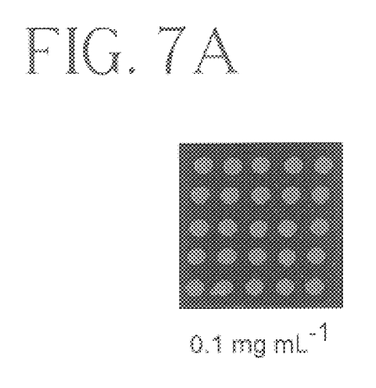
FIGS. 7A–7D are false color fluorescence images recording the hybridization of DNA to the substrate of the present invention printed with varying concentrations of DNA.
Figure 7B:
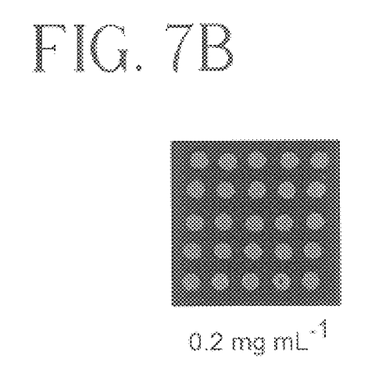
Figure 7C:
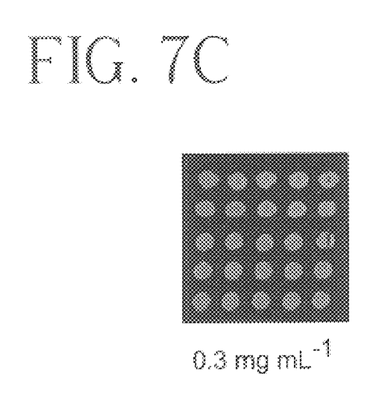
Figure 7D:
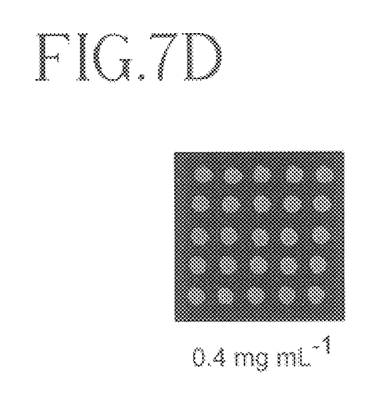

As can be readily observed, increasing the molecular weight of the polylysine on flat glass does not significantly influence either retention (FIGS. 6A–B, left side images) or hybridization (FIGS. 6A–B, right side images); the results indicate essentially similar signals for hybridization. Likewise, polylysine molecular weight appears to play little role in DNA retention on porous glass slides (FIGS. 6C–D, left side images). However, the DNA hybridization signal using the high molecular weight polylysine on porous glass (FIG. 6D, right image) is noticeably higher than lower molecular weight polylysine on porous glass (FIG. 6C, right image). It may thus be concluded that molecular weight of polylysine plays a significant role in hybridization whenusing porous glass slides. Although not intending to be limited to theory, it is believed that the longer polylysine chain of the higher molecular weight molecule is needed for porous glass in order for the polylysine to effectively extend away from the pores on the surface of the Vycor™ substrate, thereby enabling effective hybridization.

Table 2 lists signal to noise ratios calculated from the various slides. Once again, there is no appreciable difference in signal to noise between low and high molecular weight polylysine on flat glass substrates. However, while using porous glass substrates, there is an increase in signal to noise when the larger molecular weight polylysine molecule is employed.

TABLE 2

| Slide | Polylysine Mol. Wt. | Surface | Hybridization Signal (in RFU) |
|---|---|---|---|
| A | 7.5 kD | Flat glass | 1993 |
| B | 40 kD | Flat glass | 35322 |
| C | 7.5 kD | Porous glass | 28682 |
| D | 40 kD | Porous glass | 26944 |

RFU = Relative Fluorescence Units

EXAMPLE 4

Effect of DNA Concentration on Hybridization

This example demonstrates the DNA loading capacity of a substrate of the present invention over various DNA concentrations.

Soda lime glass slides were cleaned in 1M KOH solutions for 0.5 hour. After cleaning, the slides were rinsed in copious amounts of 18-ohm water and soaked in pure ethanol for 0.5 hour, and dried with nitrogen. Next, the slides were soaked in a silane solution consisting of 5% GIPS in isopropyl alcohol for approximately 2 hours in a humid chamber. The slides were then removed, briefly rinsed with isopropanol and deionized water respectively, and dried with nitrogen gas.

A bath of polylysine(7.5kD)/ethanolmine in 10 mM sodium phosphate buffer (pH 9.5–10.0) was prepared in a molar concentration of approximately 1:120. The slides were then immersed the bath solution for 45 minutes, rinsed in deionized water, and dried with nitrogen gas.

Probes in the form of 1.5 kb fragments of double stranded DNA at different concentrations (as listed in Table 3), suspended in dimethylsulphoxide: sodium citrate (DMSO:SSC) were printed in a 5×5 matrix onto each slide. Each 5×5 matrix represents DNA printed at a different concentration. After washing and blocking. Cy3 labeled complimentary target DNA fragments were hybridized to the retained DNA using standard hybridization protocols. The slides were then washed and scanned for fluorescence using a General Scanning Scanner 3000.

TABLE 3

| Slide | Concentration of DNA Printing Solution |
|---|---|
| A | 0.1 mg/ml |
| B | 0.2 mg/ml |
| C | 0.3 mg/ml |
| D | 0.4 mg/ml |

Results

FIGS. 7A–D show substantially identical hybridization signal over the range of DNA concentrations tested. Since there is no smearing effect and consistent signal at all of the DNA concentrations used for printing, it can be concluded that DNA printing is effective over at least the range tested (0.1–0.4 mg/ml).

EXAMPLE 5

Slide Effectiveness for Gene Expression Experimentation.

This example demonstrates the effectiveness of a substrate of the present invention for use in gene expression analysis.

A soda lime glass slide was cleaned in 1M KOH solutions for 0.5 hour. After cleaning, the slide was rinsed in copious amounts of 18-ohm water and soaked in pure ethanol for 0.5 hour, and dried with nitrogen. Next, the slide was soaked in a silane solution consisting of 5% GIPS in isopropyl alcohol for approximately 2 hours in a humid chamber. The slide was then removed, briefly rinsed with isopropanol and deionized water respectively, and dried with nitrogen gas.

A bath of polylysine/ethanolmine in 10 mM sodium phosphate buffer (pH 9.5–10.0) was prepared in a molar concentration of approximately 1:120. The slide was then immersed in the bath solution for 45 minutes, rinsed in deionized water and dried with nitrogen gas.

Double stranded DNA fragments representing 28 full length genes of the yeast genome were then printed onto the slide. Each gene was repetitively printed in a distinct 5×5 matrix at a concentration of 0.25 mg/ml suspended in DMSO:SSC. After washing and blocking, Cy3 labeled complimentary target DNA fragments obtained from extracted RNA from yeast were hybridized to the retained yeast gene sequences using standard hybridization protocols. The slide was then washed and scanned for fluorescence signal from hybridization using a General Scanning Scanner 3000.

Results

Figure 8:
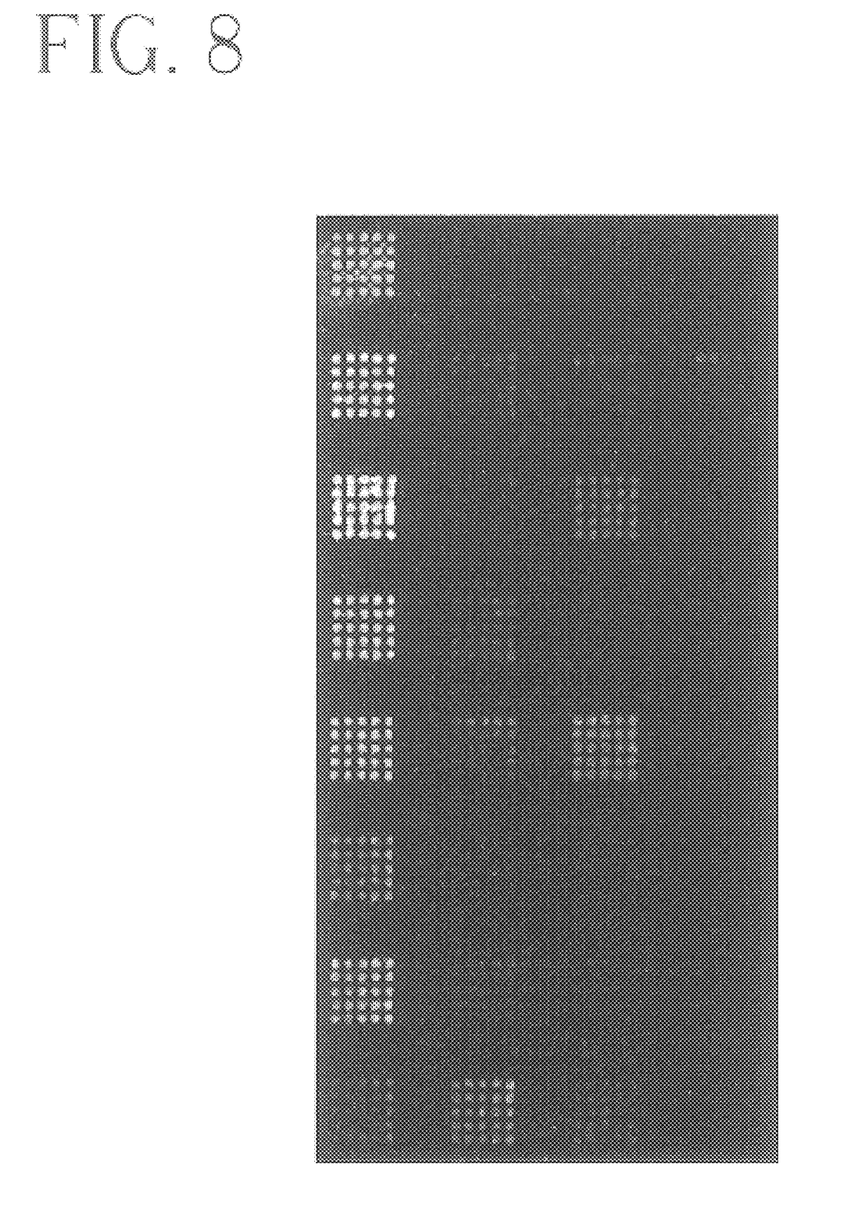
FIG. 8 is a false color fluorescence image showing the hybridization signal from Cy3 labeled yeast cDNA hybridized with 28 yeast genes of the yeast genome immobilized on the substrate of the present invention.

As can be seen from FIG. 8, gene expression levels measured from the slide may be effectively monitored. As shown in the FIG. 9, grids that are yellow and green indicate relatively high expression levels, grids that are blue indicate low levels of expression, black represents background. The ability to observe genes with different levels of expression validates the use of this surface for expression analysis. Further, within each grid, the spot to spot variability is low, demonstrating the uniformity and consistency of the polylysine/ethanalomine coating.

Although the invention has been described in detail for the purpose of illustration, it is understood that such detail is solely for that purpose and variations can no be made therein by those of skill in the art without departing from the spirit and scope of the invention which is defined by the following claims.

We claim:

1. A support for the immobilization of biomolecules, comprising:
   a) a substrate having a surface;
   b) a silane layer covalently attached to the surface; and
   c) a mixture layer a functionalized polymer including covalently attached to said silane layer 2. The support of claim 1 wherein the substrate is a glass material.

3. The support of claim 2 wherein the surface is porous.

4. The support of claim 1 wherein the silane is selected from the group consisting of isocyanatoalkysilanes, succinic anhydridealkysilanes, glycidoxyalkylsilanes, and epoxyalkysilanes.

5. The support of claim 1 wherein the functionalized polymer contains a plurality of amino groups.

6. The support of claim 1 wherein the functionalized polymer is selected from the group consisting of polylysine, polyarginine, polyethyleneimine, aminated polysaccharides, aminated oligosaccharides, polyamido amines, amino carboxylated oligosaccharides, polypeptides, and polyaminoalcohols.

7. The support of claim 1 wherein the diluent is selected from the group consisting of ethanolamine, sarcosine, glycine, and oligo(ethyleneglycol) amine.

8. The support of claim 1 further comprising a binding entity attached to the functionalized polymer layer.

9. The support of claim 8 wherein said binding entity is a nucleic acid.

10. The support of claim 1 wherein the diluent compound is ethanalomine and the functionalized polymer is polylysine and whereby the polylysine and ethanalomine are present in a predefined molar ratio with relation to each other.

11. The support of claim 10 wherein the predefined molar ratio of polylysine to ethanalomine is between 1:1 and 1:250.

12. The support of claim 10 wherein the predefined molar ratio of polylysine to ethanalomine is between 1:100 and 1:150.

13. A method of preparing a support for the immobilization of biomolecules, comprising the steps of:
   a) providing a substrate having a surface;
   b) attaching a layer of silane to the surface; and
   c) covalently attaching a mixture of functionalized polymer and diluent compound to the silane layer thereby forming a reactive outer layer adapted to attach and space biomolecules.

14. The method of claim 13 wherein the substrate is a glass material.

15. The method of claim 14 wherein the surface is porous.

16. The method of claim 13 wherein the silane is selected from the group consisting of isocyanatoalkysilanes, succinic anhydridealkysilanes, glycidoxyalkylsilanes, and epoxyalkysilanes.

17. The method of claim 13 wherein the functionalized polymer is selected from the group consisting of polylysine, polyarginine, polyethyleneimine, aminated polysaccharides, aminated oligosaccharides, polyamido amines, amino carboxylated oligosaccharides, polypeptides, and polyaminoalcohols.

18. The method of claim 13 wherein the diluent is selected from the group consisting of ethanolamine, sarcosine, glycine, and oligo(ethyleneglycol) amine.

19. The method of claim 13, further comprising the step of attaching a binding entity to the reactive outer layer.

20. The method of claim 19 wherein said binding entity is a nucleic acid.

21. The method of claim 13 wherein the diluent compound is ethanalomine and the functionalized polymer is polylyline and whereby the polylysine and ethanalomine are mixed in a predefined molar ratio with relation to each other.

22. The method of claim 21 wherein the predefined molar ratio of polylysine to ethanalomine is between 1:1 and 1:250.

23. The method of claim 22 wherein the predefined molar ratio of polylysine to ethanalomine is between 1:100 and 1:150.

24. A support for immobilizing biomolecules comprising:
   a) a substrate having a surface;
   b) a silane layer covalently attached to said surface;
   c) an outer layer comprised of a diluent compound and functionalized polymer, the outer layer covalently attached to the silane layer; and
   d) reactive esters extending from said outer layer adapted to attach and space biomolecules.

25. The support of claim 24 wherein the substrate is a glass material.

26. The support of claim 25 wherein the surface is porous.

27. 2The support of claim 24 wherein the silane is selected from the group consisting of isocyanatoalkysilanes, succinic anhydridealkysilanes, glycidoxyalkylsilanes, and epoxyalkysilanes.

28. The support of claim 24 wherein the functionalized polymer is selected from the group consisting of polylysine, polyarginine, polyethyleneimine, aminated polysaccharides, aminated oligosaccharides, polyamido amines, amino carboxylated oligosaccharides, polypeptides, and polyaminoalcohols.

29. The support of claim 24 wherein the diluent is selected from the group consisting of ethanolamine, sarcosine, glycine, and oligoethylene-glycol-amine.

30. The support of claim 24 further comprising a binding entity attached to the outer reactive layer.

31. The support of claim 30 wherein said binding entity is a nucleic acid.

32. The support of claim 24 wherein the diluent compound is ethanalomine and the functionalized polymer is polylysine and whereby then polylysine and ethanalomine are present in a predefined molar ratio with relation to each other.

33. The support of claim 32 wherein the predefined molar ratio of polylysine to ethanalomine is between 1:1 and 1:250.

34. The support of claim 32 wherein the predefined molar ratio of polylysine to ethanalomine is between 1:100 and 1:150.

35. A method for preparing a support for biomolecular immobilization, comprising:
   a) providing a substrate having a surface;
   b) attaching a silane layer to the surface;
   c) mixing a functionalized polymer interspersed with an diluent chemical compound to form a mixture for spacing immobilized biomolecules;
   d) covalently attaching the mixture to the silane layer thereby forming an outer layer;
   e) modifying the functional polymer with a cyclic anhydride, thereby creating carboxylic acid functionalities which extend from the outer layer; and
   f) reacting the carboxylic acid to form active esters extending from the outer layer adapted to attach and space biomolecules.

36. The method of claim 35 wherein the substrate is a glass material.

37. The method of claim 36 wherein the surface is porous.

38. The method of claim 35 wherein the silane is selected from the group consisting of isocyanatoalkysilanes, succinic anhydridealkysilanes, glycidoxyalkylsilanes, and epoxyalkysilanes.

39. The method of claim 35 wherein the functionalized polymer is selected from the group consisting of polylysine, polyarginine, polyethyleneimine, aminated polysaccharides, aminated oligosaccharides, polyamido amines, amino carboxylated oligosaccharides polypeptides, and polyaminoalcohols.

40. The method of claim 35 wherein the diluent is selected from the group consisting of ethanolaethanolamine, sarcosine, glycine, and oligoethylene-glycol-amine.

41. The method of claim 35 further comprising the step of attaching a binding entity to the reactive outer layer.

42. The method of claim 41 wherein said binding entity is a nucleic acid.

43. The method of claim 35 wherein the diluent compound is ethanalomine and the functionalized polymer is polylysine and whereby the polylysine and ethanalomine are mixed in a predefined molar ratio with relation to each other.

44. The method of claim 43 wherein the predefined molar ratio of polylysine to ethanalomine is between 1:1 and 1:250.

45. The method of claim 43 wherein the predefined molar ratio of polylysine to ethanalomine is between 1:100 and 1:150.

* * * * *

UNITED STATES PATENT AND TRADEMARK OFFICE
CERTIFICATE OF CORRECTION

PATENT NO. : 6,528,264 B1
DATED : March 4, 2003
INVENTOR(S) : Santona Pal et al.

It is certified that error appears in the above-identified patent and that said Letters Patent is hereby corrected as shown below:

Column 10,
Line 45, after "layer," please add -- including --.
Line 45, after "functionalized polymer", please add -- and a diluent compound for selectively spacing immobilized biomolecules, the mixture layer --

Column 11,
Line 38, delete "polylyline" and add -- polylysine --
Line 57, delete "2The" and add -- The --

Column 12,
Line 10, delete "then" and add -- the --
Line 49, delete "ethanolaethanolamine" and add -- ethanolamine --

Signed and Sealed this

Seventeenth Day of February, 2004

JON W. DUDAS
*Acting Director of the United States Patent and Trademark Office*